US00PP33303P2

(12) United States Plant Patent
Heuger

(10) Patent No.: US PP33,303 P2
(45) Date of Patent: Jul. 27, 2021

(54) ***HELLEBORUS* PLANT NAMED 'COSEH 8100'**

(50) Latin Name: ***Helleborus niger* X *Helleborus* x *hybridus***
Varietal Denomination: COSEH 8100

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,649

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 5/00; A01H 6/72
See application file for complete search history.

*Primary Examiner* — June Hwu
(74) *Attorney, Agent, or Firm* — C. Anne Whealy

(57) ABSTRACT

A new and distinct cultivar of *Helleborus* plant named 'COSEH 8100', characterized by its upright to slightly outwardly spreading and mounded plant habit; moderately vigorous growth habit; dark green-colored leaves; moderately freely flowering habit; red purple to greyed purple-colored flowers; and good garden performance.

2 Drawing Sheets

Figure 1:
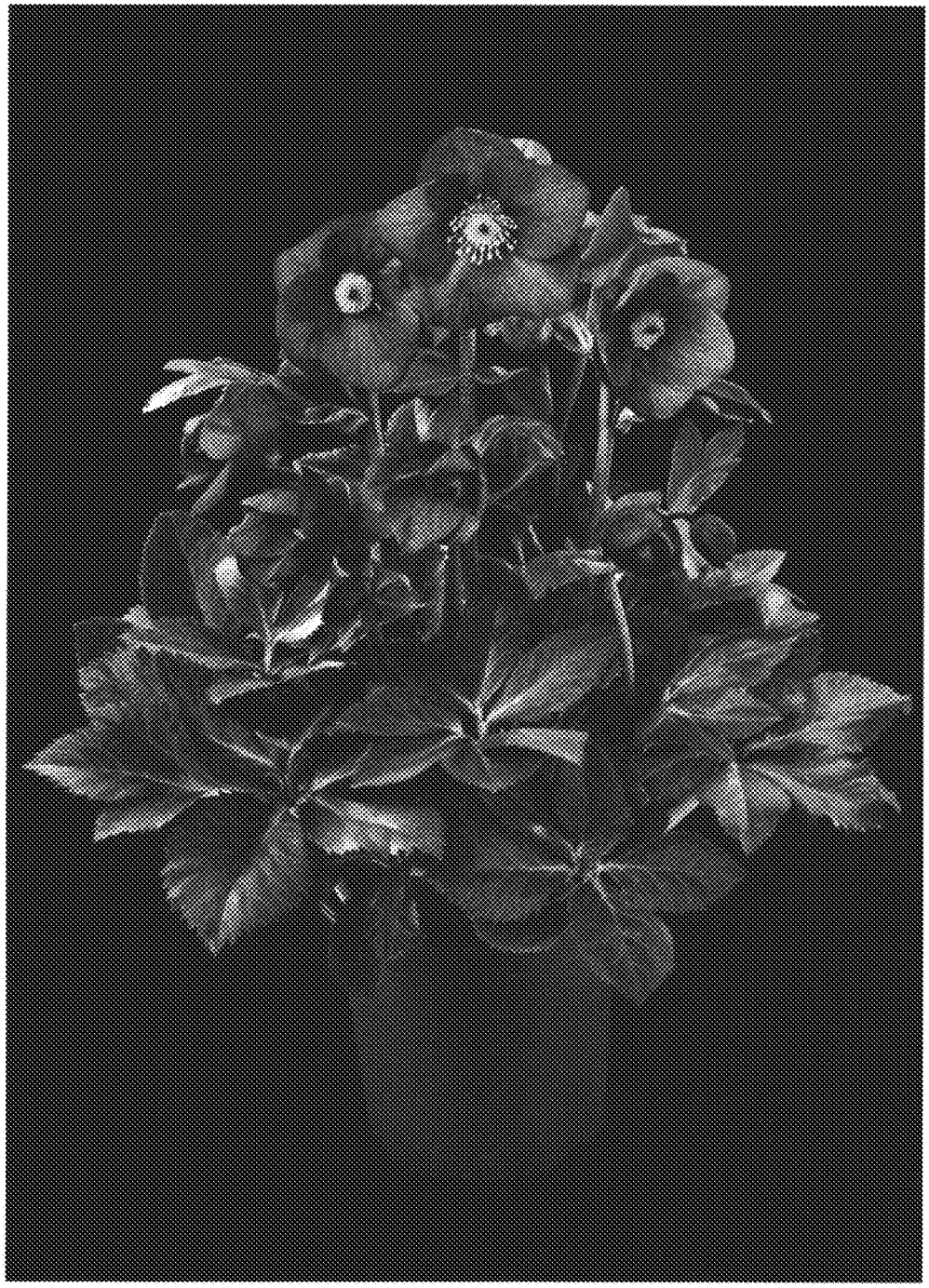

Botanical designation: *Helleborus niger* X *Helleborus* x *hybridus*.
Cultivar denomination: 'COSEH 8100'.

CROSS-REFERENCED TO CLOSELY-RELATED APPLICATIONS

Title: *Helleborus* Plant Named 'COSEH 7300'
Inventor/Applicant: Josef Heuger
Filed: Concurrently with the instant application (U.S. Plant patent application Ser. No. 16/873,636)
Title: *Helleborus* Plant Named 'COSEH 7400'
Inventor/Applicant: Josef Heuger
Filed: Concurrently with the instant application (U.S. Plant patent application Ser. No. 16/873,635)

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1395. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 8100'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a proprietary selection of *Helleborus niger* identified as code number P780, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by in vitro axillary meristem culture in a controlled environment in Glandorf, Germany since February, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 8100'. These characteristics in combination distinguish 'COSEH 8100' as a new and distinct *Helleborus* plant:

1. Upright to slightly outwardly spreading and mounded plant habit.
2. Moderately vigorous growth habit.
3 Dark green-colored leaves.

4. Moderately freely flowering habit.
5. Red purple to greyed purple-colored flowers.
6. Good garden performance.

Plants of the new *Helleborus* differ from plants of the female parent selection in the following characteristics:

1. Plants of the new *Helleborus* are more vigorous than plants of the female parent selection.
2. Flowers of plants of the new *Helleborus* are red purple to greyed purple in color whereas flowers of plants of the female parent selection are white in color.

Plants of the new *Helleborus* differ from plants of the male parent selection in the following characteristics:

1. Plants of the new *Helleborus* are more vigorous than plants of the male parent selection.
2. Flowers of plants of the new *Helleborus* are red purple to greyed purple in color whereas flowers of plants of the male parent selection are reddish in color.

Plants of the new *Helleborus* can be compared to plants of *Helleborus niger* X *Helleborus* x *hybridus* 'COSEH 7300', disclosed in a U.S. Plant Patent application filed concurrently. Plants of the new *Helleborus* differ primarily from plants of 'COSEH 7300' in flower color as plants of new *Helleborus* are red purple to greyed purple in color whereas flowers of plants of 'COSEH 7300' are dark greyed purple in color. In addition, plants of the new *Helleborus* have smaller flowers than plants of 'COSEH 7300'.

Plants of the new *Helleborus* can be compared to plants of *Helleborus niger* X *Helleborus* x *hybridus* 'COSEH 7400', disclosed in a U.S. Plant Patent application filed concurrently. Plants of the new *Helleborus* differ primarily from plants of 'COSEH 7400' in flower color as flowers of plants of the new *Helleborus* are red purple to greyed purple in color whereas flowers of plants of 'COSEH 7400' are light yellow green to white in color. In addition, plants of the new *Helleborus* have smaller flowers than plants of 'COSEH 7400'.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Plants of the new *Helleborus* differ are not as compact as plants of 'LEM 100'.
2. Plants of the new *Helleborus* are more vigorous than plants of 'LEM 100'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 8100' grown in a container.

Figure 2:
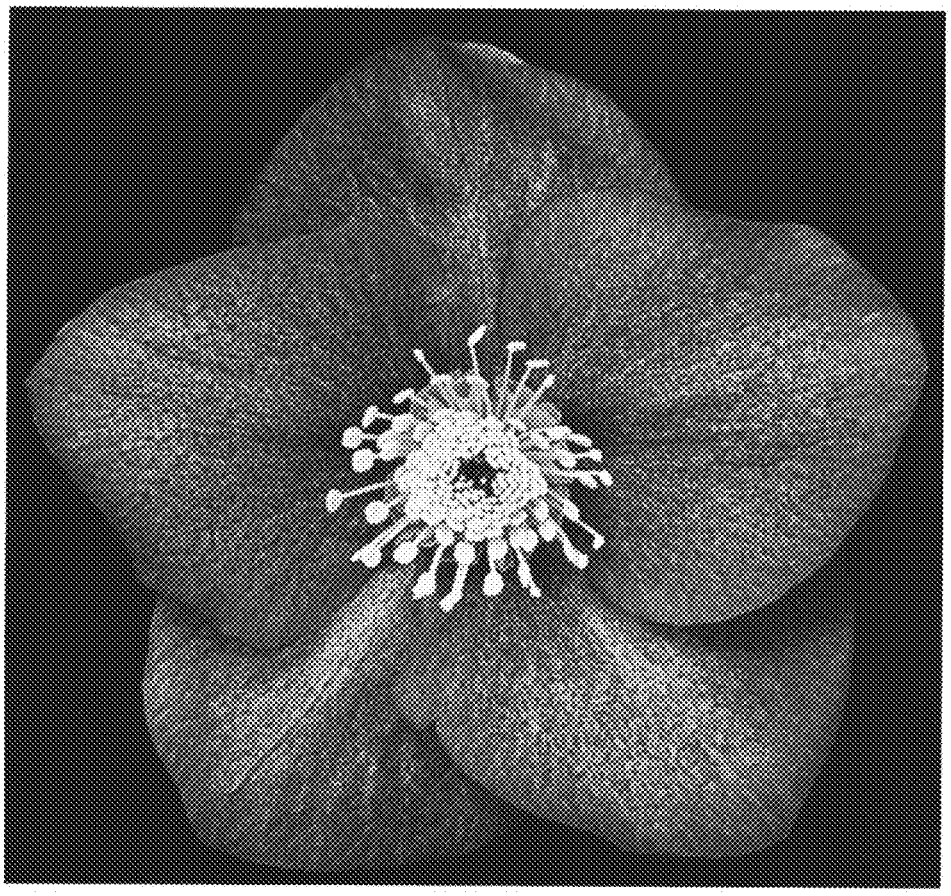

The photograph on the second sheet (FIG. 2 of 2) is a close-up view of a typical flower of 'COSEH 8100'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 8100'.

Parentage:

*Female, or seed, parent*.—Proprietary selection of *Helleborus niger* disclosed as code number P780, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held within and above the foliar plane; plant shape, broadly inverted triangular; moderately vigorous growth habit and moderate to rapid growth rate.

*Plant height, soil level to top of foliar plane*.—About 36 cm.

*Plant height, soil level to top of flowers*.—About 43 cm.

*Plant diameter* (*area of spread*).—About 55.5 cm.

Leaf description:

*Arrangement*.—Leaves arranged in a basal rosette; leaves palmately compound with typically seven leaflets per leaf.

*Leaf length*.—About 22.5 cm.

*Leaf width*.—About 22.5 cm.

*Leaflet length*.—About 12.6 cm.

*Leaflet width*.—About 6.2 cm.

*Leaf shape*.—Palmate; orbicular to reniform in outline.

*Leaflet shape*.—Obovate; lower leaflets occasionally deeply cleft.

*Leaflet apex*.—Acute.

*Leaflet base*.—Attenuate.

*Leaflet margin*.—Serrate; not undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 143A; midvein tinged at the base with close to 187A. Developing leaflets, lower surface: Close to 146B; midvein at the base, close to 183C. Fully developed leaflets, upper surface: Slightly darker than between 139A and N189A; at the base, close to between N186C and 187A; venation, close to 145A. Fully developed leaflets, lower surface: Close to 147B; venation, close to 143C and at the base, close to 183A to 183B.

*Petioles*.—Length: About 22 cm. Diameter: About 8 mm to 10 mm. Strength: Strong. Texture and luster, upper and lower surfaces: Smooth, glabrous; moderately glossy. Color, upper and lower surfaces: Close to 144A moderately covered with fine dots, close to 183A; proximally, heavily covered with fine dots, close to 187A; distally, heavily covered with fine dots, close to 178A.

Flower description:

*Flower shape and habit*.—Rotate flowers; flowers slightly to moderately cupped; arranged in panicles; moderately freely flowering habit with about two flowers per inflorescence and about 20 flowers developing per plant; flowers face mostly outwardly to slightly nodding and slightly upright.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 2.5 cm. Diameter: About 1.3 cm. Shape: Narrowly ovate. Texture and luster: Smooth, glabrous; matte. Color: Close to 145B; towards the apex, strongly tinted with close to 59D; venation, close to 61A.

*Inflorescence height* (*including peduncle*).—About 44.1 cm.

*Inflorescence diameter*.—About 13.6 cm.

*Flower diameter*.—About 7.4 cm by 7.4 cm.

*Flower depth* (*height*).—About 2.5 cm.

*Petals*.—All petals are transformed into nectaries.

*Sepals*.—Quantity and arrangement: About five, arranged in a single whorl. Length: About 4 cm. Width: About 3.5 cm. Shape: Broadly ovate, slightly concave. Apex: Obtuse. Base: Truncate to rounded. Margin: Entire; slightly undulate. Texture and luster, upper and lower surfaces: Smooth, glabrous; matte. Color: When opening, upper surface: Close to 71A finely dotted and splashed with close to 70A to 70D; at the base, close to 144C. When opening, lower surface: Close to 60C; at the base, tinged with close to 178A; venation, close to 59A. Fully opened, upper surface: Close to 70A finely dotted and splashed with close to 187A; at the base, close to 146C; venation, similar to lamina; with development, color becoming closer to 147B finely dotted with close to 200B. Fully opened, lower surface: Close to 60C finely dotted and splashed with close to 187A; at the base, close to 146C; venation, close to 59A; with development, color becoming closer to between 147B and 148A and venation, close to N186C.

*Flower bracts*.—Quantity per flower: Typically one or two. Length: About 4.2 cm. Width: About 2.7 cm. Shape: Ovate to broadly ovate. Apex: Acute. Base: Truncate. Margin: Sparsely and shallowly dentate to serrate; coarsely undulate. Color, upper surface: Close to between NN137A and 139A; venation, similar to lamina. Color, lower surface: Close to 138A; venation, close to 187A to 187B.

*Peduncles*.—Length: About 37.1 cm. Diameter: About 7 mm to 8 mm. Aspect: About 10° from vertical. Strength: Strong. Texture and luster: Smooth, glabrous; slightly glossy. Color: Close to 146C, heavily covered with fine dots, close to 187A.

*Pedicels*.—Length: About 6.6 cm. Diameter: About 3 mm. Aspect: About 10° to 40° from peduncle axis. Strength: Moderately strong. Texture and luster: Smooth, glabrous; moderately glossy. Color: Close to 146C heavily covered with fine dots, close to 187A to 187B.

*Reproductive organs*.—Stamens: Quantity per flower: About 100. Filament length: About 1.6 cm. Filament color: Close to 155B. Anther shape: Double and broadly reniform; basifixed. Anther size: About 1.75 mm by 2 mm. Anther color: Close to 150C. Pollen amount: Sparse to moderate. Pollen color: Close to 4D to lighter than 4D. Pistils: Quantity per flower: About seven to ten. Pistil length: About 1 cm. Stigma diameter: About 0.3 mm. Stigma shape: Club-shaped. Stigma color: Slightly lighter than 150D. Style length: About 9 mm. Style color: Close to 187B. Ovary color: Close to 145A to 145B. Nectaries (transformed petals): Quantity per flower: About 18. Length: About 1.2 cm. Diameter: About 3.5 mm. Shape: Tubular, flattened. Texture and luster, inner and outer surfaces: Smooth, glabrous; slightly glossy. Color, immature, inner surface: Close to 145B. Color, immature, outer surface: Close to 145B; basal spot, close to 166A. Color, mature, inner surface: Close to 144A; towards the apex, close to N144B; venation, similar to lamina; color does not change with development. Color, mature, outer surface: Close to 144A; towards the apex, close to N144B; basal spot, close to 166A; venation, similar to lamina; color does not change with development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 8100' as illustrated and described.

* * * * *